(12) United States Patent
Allen

(10) Patent No.: US 7,402,147 B1
(45) Date of Patent: Jul. 22, 2008

(54) BODY LIMB MOVEMENT LIMITER

(76) Inventor: Susan Davis Allen, 418 W. Matthews Ave., Jonosboro, FL (US) 72401

( * ) Notice: Subject to any disclaimer, the term of this patent is extended or adjusted under 35 U.S.C. 154(b) by 304 days.

(21) Appl. No.: 11/099,381

(22) Filed: Apr. 4, 2005

Related U.S. Application Data

(63) Continuation-in-part of application No. 09/992,611, filed on Nov. 19, 2001, now abandoned.

(60) Provisional application No. 60/249,312, filed on Nov. 17, 2000.

(51) Int. Cl.
*A61F 5/00* (2006.01)

(52) U.S. Cl. .................. 602/20; 602/5; 602/19

(58) Field of Classification Search ............ 602/5, 602/19, 20, 26, 16; 128/869, 876, 878, 873, 128/874, 875; 473/450; 273/317.2
See application file for complete search history.

(56) References Cited

U.S. PATENT DOCUMENTS

| | | | |
|---|---|---|---|
| 2,773,691 A | 12/1956 | Redfield | |
| 3,104,650 A * | 9/1963 | Grahling | 119/770 |
| 4,088,201 A | 5/1978 | MacFarlane | |
| 4,441,707 A | 4/1984 | Bosch | |
| 4,480,716 A | 11/1984 | Soubry et al. | |
| 4,508,285 A | 4/1985 | McMillan | |
| 4,621,589 A * | 11/1986 | Thinnes | 119/770 |
| 5,188,365 A | 2/1993 | Picard | |
| 5,358,461 A | 10/1994 | Bailey, Jr. | |
| 5,558,102 A | 9/1996 | McCarthy | |
| 5,599,290 A | 2/1997 | Hayes et al. | |
| 5,704,856 A | 1/1998 | Morse | |
| 5,712,011 A | 1/1998 | McMahon et al. | |
| 5,733,231 A | 3/1998 | Corn et al. | |
| 5,758,839 A | 6/1998 | Kim | |
| 5,776,839 A | 7/1998 | Dischler et al. | |
| 6,095,936 A | 8/2000 | Kirkpatrick et al. | |
| 6,099,447 A | 8/2000 | Ramsaroop | |
| 6,126,554 A | 10/2000 | Poscente | |
| 6,138,677 A | 10/2000 | DeVane | |

* cited by examiner

*Primary Examiner*—Kim M Lewis
(74) *Attorney, Agent, or Firm*—Peter Loffler

(57) ABSTRACT

A body limb movement limiter restrains the movement of a person's arm so as to protect the person's shoulder or restrains the movement of a person's lower leg with respect to the upper leg so as to protect the person's knee. The device uses a housing having a reel disposed therein with a tether attached thereto and a shear thickening non-Newtonian fluid disposed within the housing so that the fluid acts on the reel during a payout procedure of the tether. The housing is attached to a strap secured about the torso of the person while the free end of the tether is secured about the person's arm. Alternately, a pair of arms are pivotally secured to each other within a housing having the non-Newtonian fluid therein for limiting movement of one arm with respect to the other.

7 Claims, 7 Drawing Sheets

BODY LIMB MOVEMENT LIMITER

This application is a cip of U.S. patent application Ser. No. 09/992,611, filed on Nov. 19, 2001, now abandoned, which itself claims the benefit of U.S. Provisional Patent Application 60/249,312, filed on Nov. 17, 2000.

BACKGROUND OF THE INVENTION

1. Field of the Invention

The present invention relates to a body limb movement limiter that uses a non-Newtonian fluid so as to prevent sudden rapid movement of a person's arm or leg, or other joint, thereby preventing injury to the person's injury-recovering joint.

2. Background of the Prior Art

In recovering from an injury to the shoulder, knee, or other joint, with or without surgery to the joint, slow and gradual use of the affected area is desired in order to build strength and prevent shortening of the affected tendon or ligament. If the joint is subjected to sudden rapid forces the healing process to the affected area can be compromised resulting in a slowing of the healing of the affected area, reinjury, or further damage to the affected area which can result in the need for additional medical intervention. This not only results in further discomfort to the patient but slows the overall healing and recovery time.

Devices have been proposed that help limit movement of a person's joint such as the shoulder, knee, elbow, ankle, hip, etc., so as to prevent the patient from subjecting the joint to sudden rapid acceleration and consequent forces on the affected area. Such devices help prevent the attendant damage that can result from such rapid acceleration and work with varying degrees of efficiency.

The problem with the movement limiting devices found in the art is that such devices, being linear in their deceleration capacity, limit the normal and desired movements of a user of such devices. Such devices fail to discriminate between a desired normal movement associated with the joint and an undesired rapid movement than can cause damage to the user. These devices tend to make many normal movements, such as walking or carrying groceries relatively uncomfortable. While such discomforts may be an acceptable tradeoff to some, for the benefit of minimizing damage resulting from undesired rapid acceleration, these discomforts are less than ideal.

Other prior art devices will allow normal movement associated with a shoulder or a knee to a point and once that point is surpassed, a braking action is applied. While these devices will prevent much of the damage associated with full rapid acceleration of the affected area, the sudden braking action can cause a jerking force on the shoulder or knee, which can result in undue discomfort or some amount of damage to the tendons or ligaments thereat.

Therefore, there exists a need in the art for a device that will prevent rapid movement associated with a person's shoulder or knee or other joint. Such a device will allow the user to perform normal desirable functions without undue discomfort, yet will prevent sudden rapid acceleration of a person's limb, resulting in pain, reinjury or damage to the person's joint. The deceleration provided by such a device must be gradual so as not to exert a jerking force onto the user's affected area. Ideally, such a device must be of relatively simple design and construction and must be relatively easy to don and use.

SUMMARY OF THE INVENTION

The body limb movement limiter of the present invention addresses the aforementioned needs in the art. The body limb movement limiter is worn by a user and helps prevent the sudden rapid movement of a person's limb in order to protect a recuperating joint associated with the limb. The deceleration provided by the device is gradual and corresponds to the attempted force exertion of the limb which the device is decelerating. The device does not impose a sudden jerking force on the targeted limb. The body limb movement limiter of the present invention is of relatively simple design and construction and is relatively easy to don and use.

The present invention relies on the properties of shear thickening or dilatant non-Newtonian fluid for smooth and gradual braking action. In an ideally viscous system, a fluid exhibits Newtonian flow behavior wherein a linear relationship exists between shear stress and shear rate where the coefficient of viscosity is the constant of proportionality. The viscosity of the fluid is constant over the measured range of shear rates. On the other hand, a non-Newtonian fluid exhibits nonlinear characteristics, which can be described by several different types of behavior.

One of the three most common types of non-Newtonian fluid behavior is shear thinning or pseudoplastic. With increasing shear rate, the viscosity of the fluid decreases. This is the most common type of non-Newtonian fluid behavior. Pseudoplastic behavior is a highly desirable trait for many materials including inks, extrusion materials, and paints. For example, modern paints exhibit high viscosity at rest when a brush is dipped into the paint, thereby allowing the brush to pick up and carry a significant amount of the paint. However, as the shear rate increases, due to brushing, the viscosity is decreased allowing a thin, even layer of paint to be applied to the surface being brushed. One major class of chemicals that exhibits pseudoplastic behavior is the dimethylsiloxanes and other silicone chemicals as shown in the viscosity vs. shear rate graph for a manufacturer of such silicones, United Chemical Technologies, of Bristol, Pa. —http://www.united-chem.com/PDF/petrarch%205.pdf at page 237.

Another common type of non-Newtonian fluid behavior is known as shear thickening or dilatant. With increasing shear rate, the viscosity of the fluid increases. This type of behavior is uncommon, but is finding increased usage in various applications. The most common example of a shear thickening or dilatant non-Newtonian fluid is a concentrated mixture of cornstarch and water. In most industrial processes, shear thickening is undesirable as it tends to cause equipment that is handling materials with high particulate loading to freeze up.

A third common, albeit the least common of the three major types, is known as Bingham plasticity. At low shear rates, the material behaves as a solid. Above a "yield stress," the material is essential Newtonian. One of the most common examples of this type of behavior is toothpaste.

The body limb movement limiter of the present invention, as applied to a person suffering a shoulder or knee injury, is comprised of a housing having an opening and a reel rotatably disposed therein. A tether having a first end is attached to the reel and a second end located external of the opening, the tether wound about the reel. A shear thickening or dilatant non-Newtonian fluid is disposed within the housing and acts upon the reel during unwinding of the reel. A first strap is attached to the housing and is adapted to be secured about the torso of a person. The non-Newtonian fluid acts as a gradual brake due to the fact that the viscosity of the fluid increases as the force applied to a member within the fluid increases. A first closure means, such as cooperating hook and loop material, is provided for securing the ends of the first strap together. A second strap is attached to the second end of the tether and is adapted to be secured about an arm of the person. A second closure means, such as cooperating hook and loop material, is provided for securing the ends of the second strap together. The tether is comprised of a first section removably secured to a second section. The housing is comprised of a first chamber and a second chamber fluidly sealed from the first chamber and such that the reel is disposed within the first chamber and a rotor is disposed within the second chamber such that the rotor is mechanically connected to the reel such that rotation of the reel causes rotation of the rotor and wherein the shear thickening non-Newtonian fluid is disposed within the second chamber. Alternately, the body limb movement limiter can be comprised of a first housing and a first arm having a first end disposed within the first housing and a second end. A second arm having a third end is pivotally attached to the first end of the first arm, and has a fourth end. A shear thickening non-Newtonian fluid is disposed within the first housing and acts on the first arm during movement of the first arm with respect to the second arm. A second housing has a third arm having a fifth end disposed within the second housing and a sixth end. A fourth arm having a seventh end is pivotally attached to the fifth end of the third arm, and has an eight end. A non-Newtonian fluid is also disposed within the second housing and acts on the third arm during movement of the third arm with respect to the fourth arm. A first stabilizer connects the first housing with the second housing. The first housing is comprised of a first chamber and a second chamber fluidly sealed from the first chamber and such that the first arm is disposed within the first chamber and a first rotor is disposed within the second chamber such that the first rotor is mechanically connected to the first arm such that movement of the first arm causes movement of the first rotor and wherein the non-Newtonian fluid is disposed within the second chamber and the second housing is comprised of a third chamber and a fourth chamber fluidly sealed from the third chamber and such that the third arm is disposed within the third chamber and a second rotor is disposed within the fourth chamber such that the second rotor is mechanically connected to the third arm such that movement of the third arm causes movement of the second rotor and wherein the non-Newtonian fluid is disposed within the fourth chamber. A first strap connects the first arm with the third arm while a second strap connects the second arm with the fourth arm. A second stabilizer connects the second arm with the fourth arm.

BRIEF DESCRIPTION OF THE DRAWINGS

Similar reference numerals refer to similar parts throughout the several views of the drawings.

DESCRIPTION OF THE PREFERRED EMBODIMENT

Figure 1A:
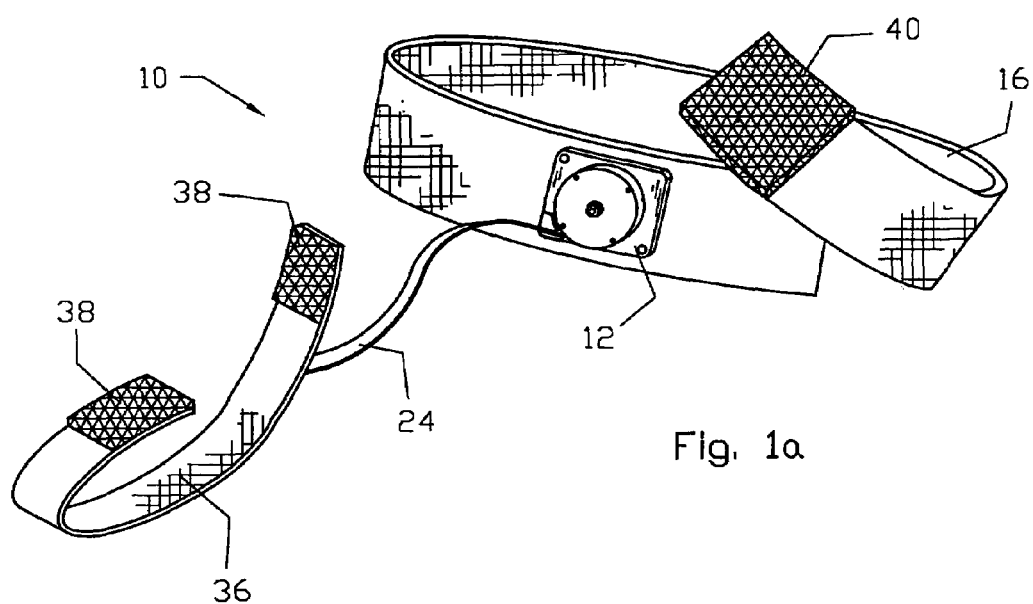
FIG. 1a is a perspective view of the body limb movement limiter for limiting movement of the upper arm region.
Figure 1B:
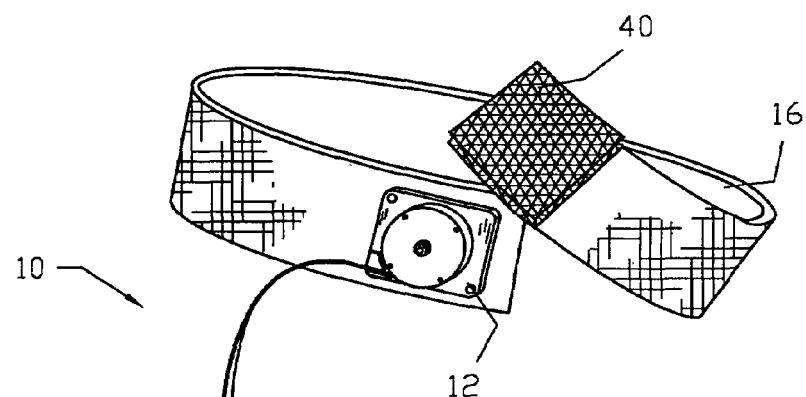
FIG. 1b is a perspective view of the body limb movement limiter for limiting movement of the lower arm region.
Figure 1B:
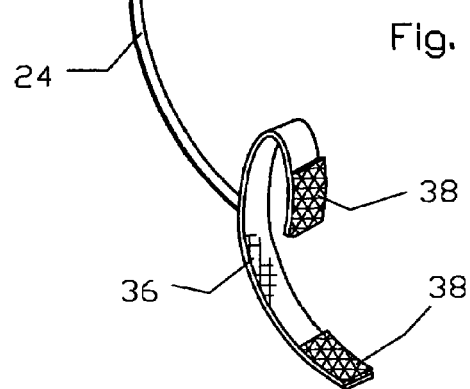
Figure 2A:
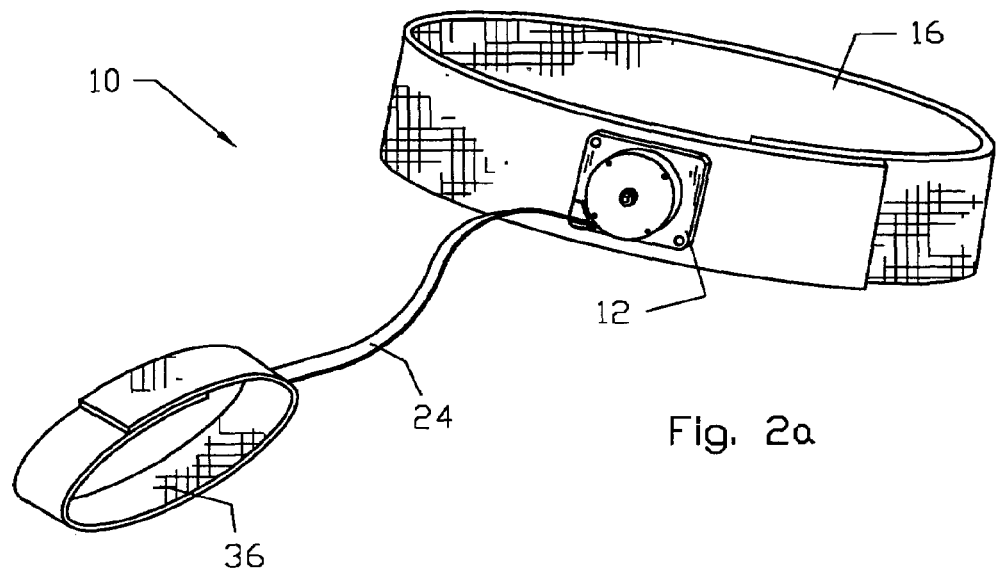
FIG. 2a is a perspective view of the body limb movement limiter for limiting movement of the upper arm region wherein the body strap and the arm band are both closed.
Figure 2B:
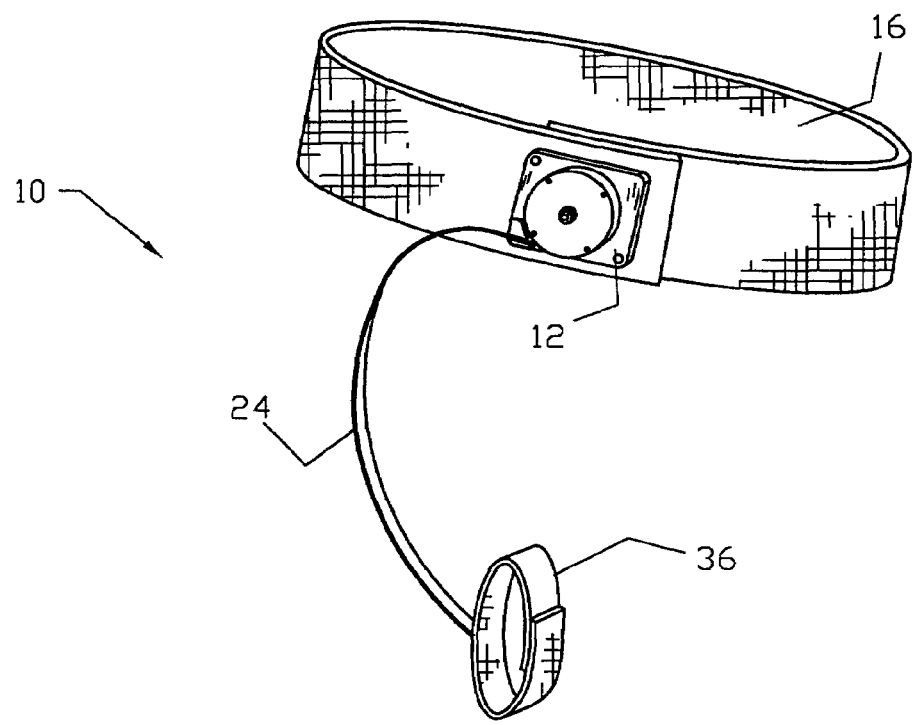
FIG. 2b is a perspective view of the body limb movement limiter for limiting movement of the lower arm region wherein the body strap and the arm band are both closed.

Referring now to the drawings, it is seen that the body limb movement limiter of the present invention, generally denoted by reference numeral 10, is comprised of a limiter housing 12, having a cover 14 for access to the interior thereof, the housing 12 being attached to a strap 16 dimensioned to either fit about the chest of a user, as seen in FIGS. 1a and 2a or the strap 16 is dimensioned to fit about the waist of a user, as seen in FIGS. 1b and 2b.

Figure 3:
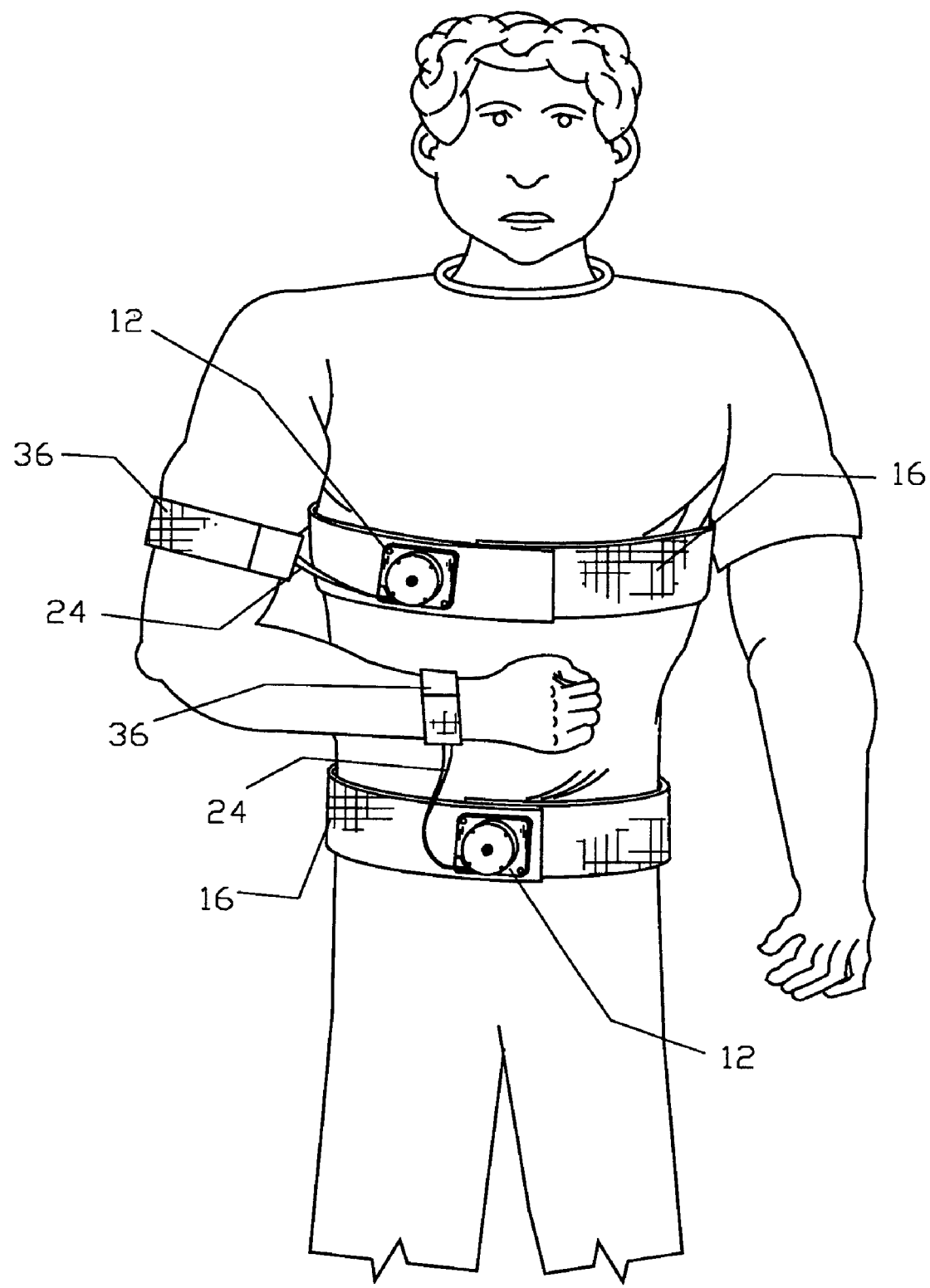
FIG. 3 is an environmental view of the body limb movement limiter showing the embodiments of FIGS. 1a and 1b secured to a user.
Figure 4:
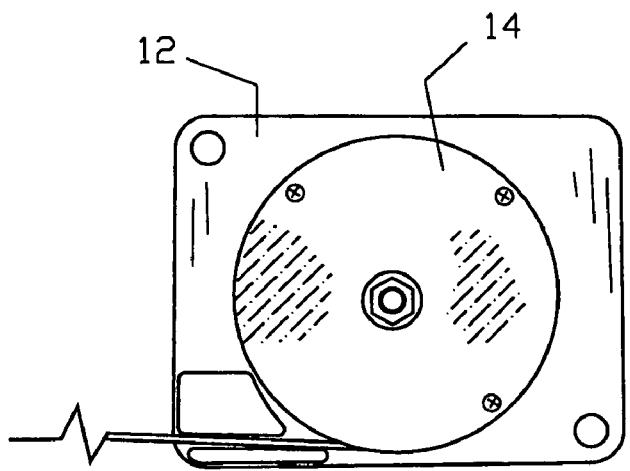
FIG. 4 is an elevation view of the limiter housing.
Figure 5:
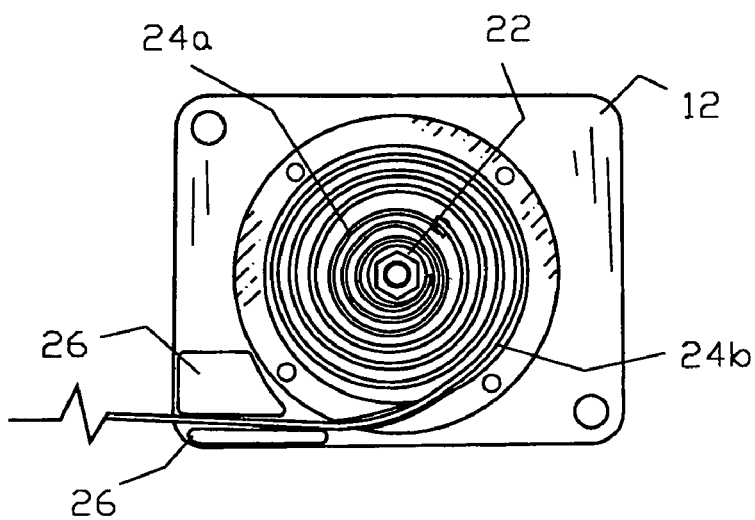
FIG. 5 is an elevation view of the limiter housing having the cover removed.
Figure 6:
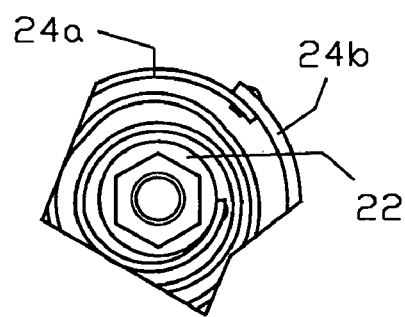
FIG. 6 is a close-up view of the two tether sections connected together within the limiter housing.
Figure 7:
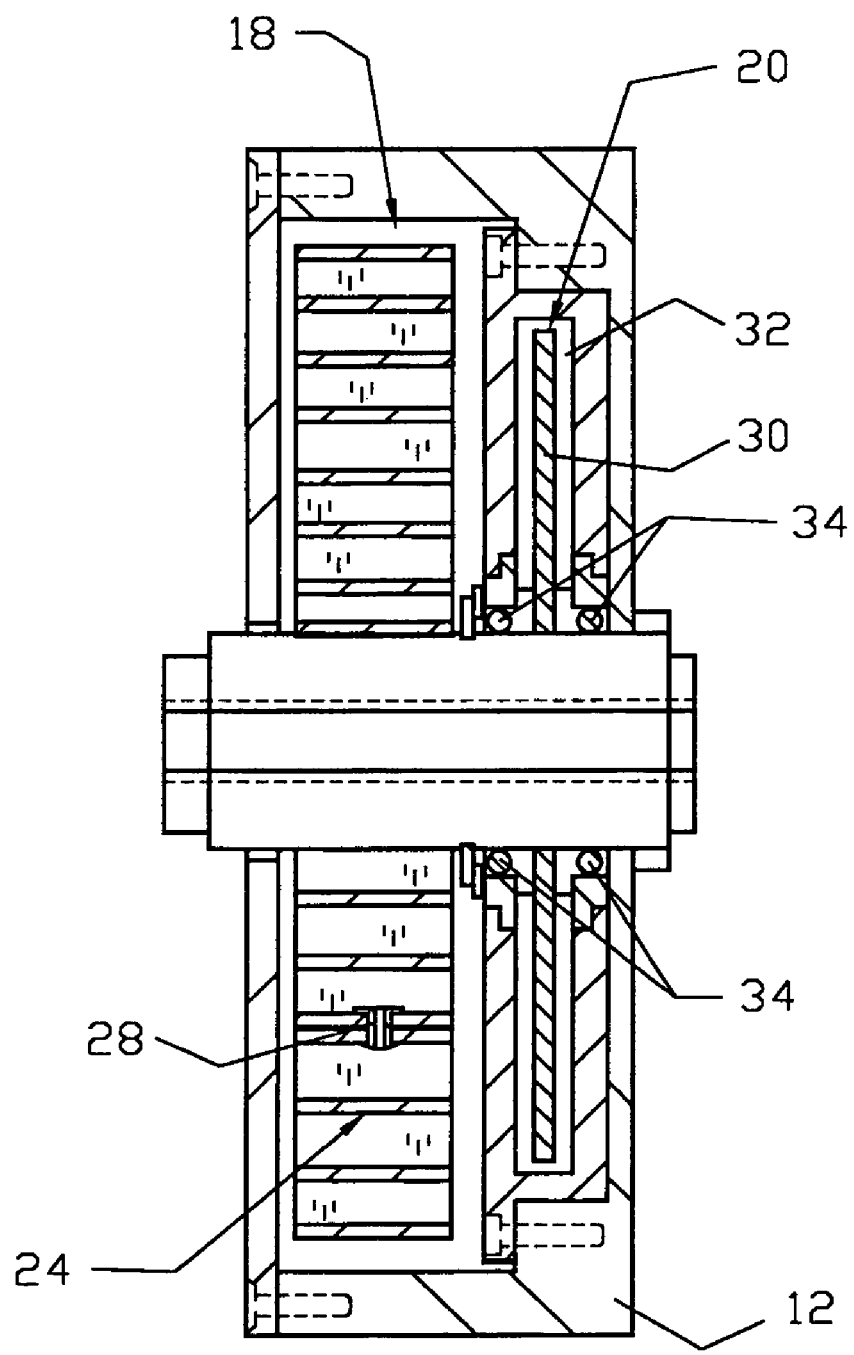
FIG. 7 is a sectioned view of the housing.

A first chamber 18 and a second chamber 20 are each located within the housing 12. A take-up reel 22 is rotatably disposed within the housing 12 and passes through the two chambers 18 and 20. A tether 24 has a first end that is connected to the take-up reel 22 and has a second end that is located exterior of the housing 12 and passes through guides 26 located at the opening of the housing 12. As seen, the tether 24 may be comprised of a first section 24a and a second section 24b such that a connector 28 of any appropriate design connects the two sections 24a and 24b. The take-up reel 22 has an automatic take-up mechanism (not illustrated) of any design commonly found in the art such that whenever the tether 24 is unwound from the take-up reel 22, the take-up mechanism causes the take-up reel 22 to automatically rewind the tether 24 onto the take-up reel 22. Disposed within the second chamber 20, a rotor 30 is also connected to the take-up reel 22 and rotates with the rotation of the take-up reel 22. A non-Newtonian fluid 32 is also disposed within the second chamber 20 and substantially fills the second chamber 20. A pair of O-rings 34 prevents the non-Newtonian fluid 32 from escaping from the second chamber 20. The non-Newtonian fluids of interest for this application are those which increase in viscosity with increasing shear forces. A band 36 is connected to the free end of the tether 24. The band 36 is dimensioned to fit about a user's upper arm as seen in FIGS. 1a, 2a, and 3, or the band 36 is dimensioned to fit about the user's lower arm as seen in FIGS. 1b, 2b, and 3. A first closure mechanism 38 secures the two ends of the band together. The first closure mechanism 38 can be of any appropriate design such as the illustrated cooperating hook and loop material.

In use, the strap 16 is fit either about the user's chest or about the user's waist. The strap 16 is secured in place by providing a second closure mechanism 40. The second closure mechanism 40 can be of any appropriate design such as the illustrated cooperating hook and loop material. The band 36 is placed around the appropriate portion of the user's arm—either about the user's upper arm if the strap 16 is placed around the user's chest, or about the user's lower arm if the strap 16 is placed about the user's waist. For use together, a wide strap with over-the shoulder stabilizing straps accommodates both mechanisms.

As the fluid 32 disposed within the second chamber 20 is a shear thickening non-Newtonian fluid, the more force applied to the rotor 30, the more viscous the fluid 32 becomes and the more friction the fluid 32 exerts on the rotor 30 thereby tending to dampen the rotation of the rotor 30. Therefore, if the user moves his arm away from his body in a slow fashion, the take-up reel 22 and the connected rotor 30 will be rotated, via the tether 24 connected to the take-up reel 22, relatively slowly, and the frictional damping placed on the rotor 30 by the fluid 32 will be relatively small. However, if the user moves his arm suddenly and quickly away from his body, the user's pull on the take-up reel 22 and the rotor 30 will be relatively strong. As the rotor 30 is disposed within the fluid 32, the increased force exerted on the rotor 30 results in more frictional dampening by the fluid 32 against the rotor 30. This results in a braking action on the take-up reel 22 preventing the user from the desired quick movement of his arm. The braking action will be gradual so as to prevent a jerk on the take-up reel 22 and thus on the user's arm. Therefore, a user who is suffering from an arm or shoulder injury or other condition will be prevented from rapid high acceleration movements of the arm, thereby tending to eliminate injury to the healing tendons and ligaments that can be occasioned from such a sudden movement of the arm. As the braking action is soft and gradual, the arm will not be jerked to a stop and thus injury from such a jerk stop will be avoided.

The take-up of the tether 24 upon the take-up reel 22 will be controlled by the take-up mechanism. The take-up mechanism is designed so as not to perform the take-up operation too fast. Additionally, the user tends to make the return movement of his arm back to his body much more consciously, therefore, the gradual braking action provided by the device 10 is not necessary for the return of the arm.

As the tether 24 is in two sections 24a and 24b, the two sections can be made from separate material. Additionally, whenever the second section 24b becomes worn or otherwise needs to be replaced, the second section 24b can be detached from the first section 24a and a new section reattached external of the housing 12, thereby eliminating the need to disassemble the device 10 in order to effect a second section 24b replacement. The maximum pay out of the tether 24 from the take-up reel 22 is a human arm's length which is the length as measured between the strap 16 and the band 36 when the arm of the user that has the band 36 thereon is fully extended in a direction that is opposite the housing 12.

Figure 8:
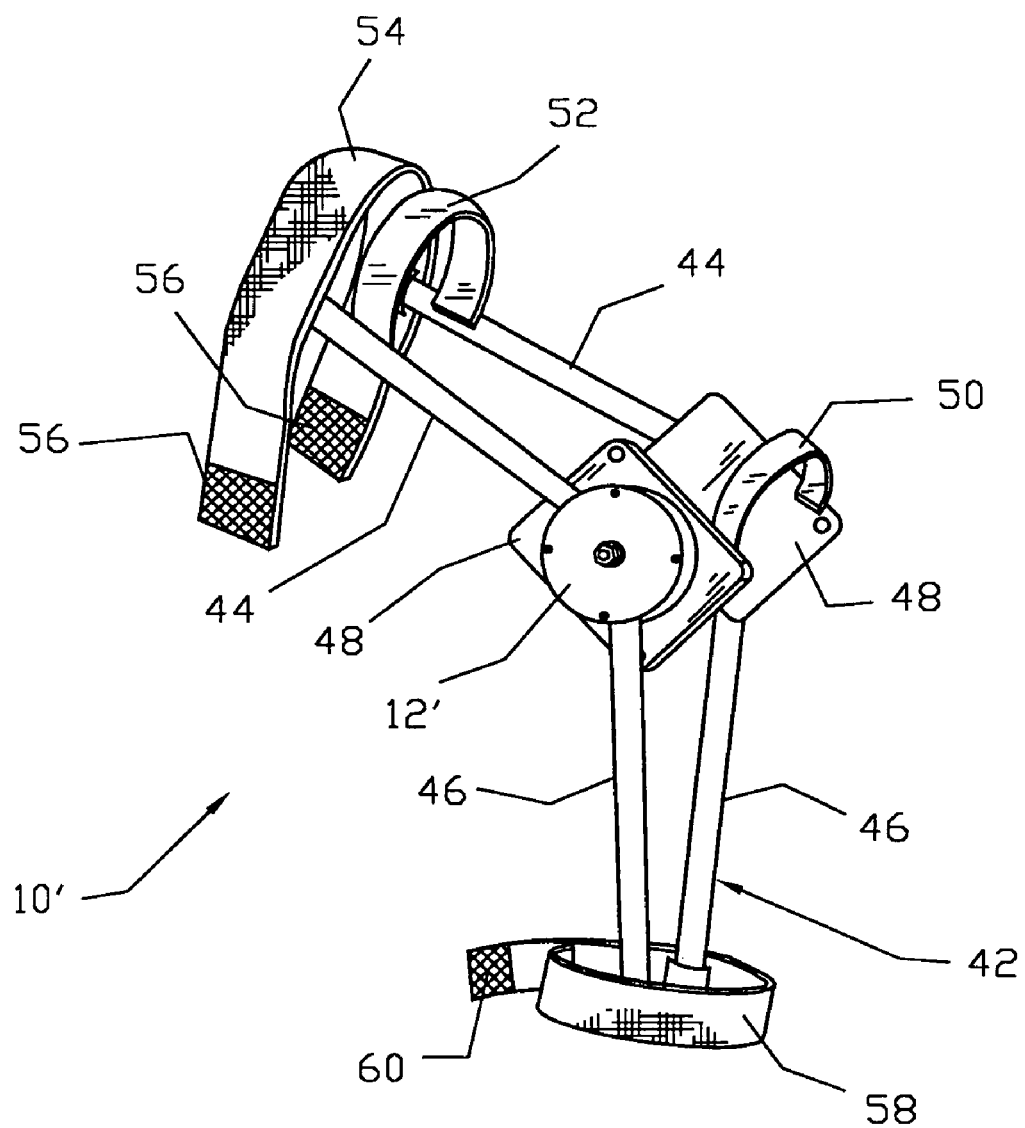
FIG. 8 is a perspective view of the body limb movement limiter for limiting movement of the lower leg region.
Figure 9:
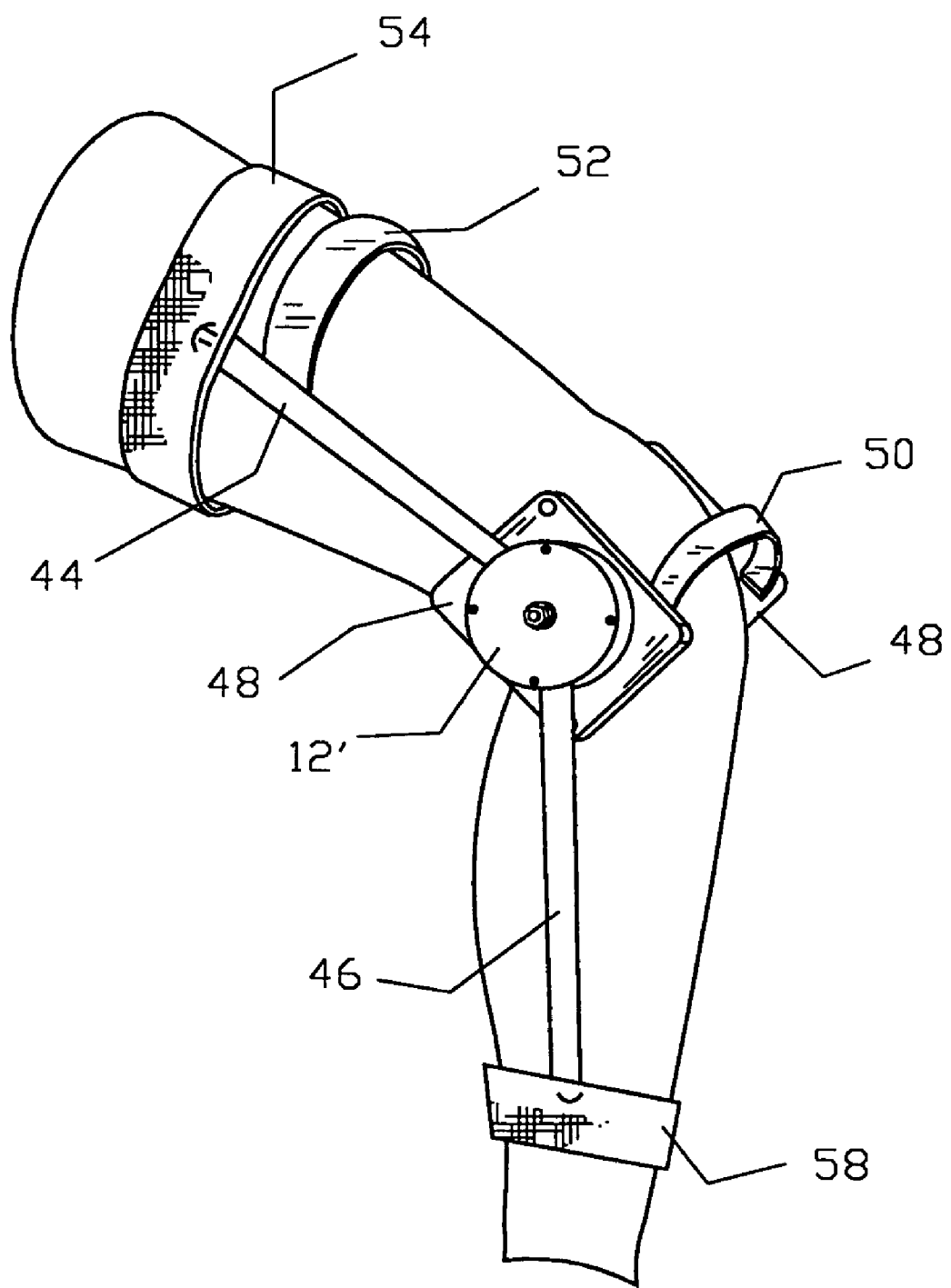
FIG. 9 is an environmental view of the body limb movement limiter of FIG. 8 secured to a user.

As seen in FIGS. 8 and 9, the body limb movement limiter 10' of the present invention can also be used to prevent sudden and quick movements of the lower leg of the user. Such a device 10' is comprised of a brace 42 that has a pair of upper arms 44 and a pair of lower arms 46. A pair of plates 48 is provided and is connected together by a first stabilizer 50. Located on each of the plates 48 is a housing 12' such that one of the upper arms 44 is hingedly connected to a corresponding lower arm 46 within one of the housings 12' and the other upper arm 44, lower arm 46 pair is hingedly connected to each other within the other housing 12'. The lower arm 46 is connected to a rotor (not illustrated), the rotor disposed within a chamber within the housing, the chamber having a shear thickening non-Newtonian fluid substantially filling the chamber. The rotor moves in lockstep with movement of the lower arm 46 to which it is attached. Therefore, the faster the attempted acceleration of the lower arm 46, —corresponding to rapid attempted acceleration of the lower leg of the user— the more viscous the non-Newtonian fluid becomes and the more frictional dampening placed onto the rotor by the fluid, resulting in gradual braking of the lower arm 46 and thus the lower leg of the user. This arrangement prevents rapid acceleration of both forward lower leg movement and rearward leg movement. The brace 42 is placed onto the user such that a second stabilizer 52 that connects the two upper arms 44, rests on the upper surface of the user's thigh. A first strap 54 is wrapped around the thigh and the first strap 54 is connected to itself by an appropriate closure mechanism 56 such as the illustrated hook and loop material. A second strap 58 is wrapped around the lower leg of the user and the second strap 58 is secured to itself by an appropriate closure mechanism 60 such as the illustrated hook and loop material. If desired, some or all components of the brace 42 are padded for increased user comfort.

The use of relatively small tether payout used with the present invention 10 can be modified for use as a vehicular seat belt payout system wherein the seat belt strap acts as the tether and is wound about the take-up reel which is connected to a rotor disposed within the shear thickening non-Newtonian fluid. In such an embodiment, at relatively low shear rates, such as when a person buckled in by the seat belts moves about—to change the stereo settings for example—the take-up reel pays out the seat belt strap in relatively normal fashion. However, at high shear rates, such as when the seat belt is suddenly and violently jerked during a vehicular crash, the viscosity of the shear thickening non-Newtonian fluid increases causing a gradual breaking on the seat belt strap and preventing the occupant from hitting the windshield or dashboard while, due to the gradual braking action of the non-Newtonian fluid, also preventing a serious impact injury caused by a complete and sudden jerk stop of the strap upon the person's upper torso region.

While the preferred embodiment employs a shear thickening non-Newtonian fluid to produce a body limb movement limiter that requires no external power source, other means of preventing the forces generated by rapid acceleration can be employed, such as a combination of acceleration sensing and "soft" or dampened braking achievable by electrically driven clamps or electrically or magnetically modified fluid viscosity.

While the invention has been particularly shown and described with reference to embodiments thereof, it will be appreciated by those skilled in the art that various changes in form and detail may be made without departing from the spirit and scope of the invention.

I claim:

1. A method of limiting the movement of a person's limb comprising the steps of:
    providing a housing having an opening and a reel rotatably disposed therein and securing the housing to the person;
    providing a tether having a first end and a second end;
    attaching the first end of the tether to the reel, winding the tether about the reel, and securing the second end of the tether to the person's limb; and
    placing a shear thickening non-Newtonian fluid within the housing for acting on the reel whenever the tether pays out from the housing and such that the pay out of the tether from the housing is decelerated.

2. The method as in claim 1 further comprising the steps of:
    wherein the step of securing the housing to the person comprises providing a first strap and attaching the housing to the first strap; and
    securing the first strap about the torso of the person.

3. The method as in claim 2 further comprising a closure means for securing the ends of the first strap together.

4. The method as in claim 2 further comprising the steps of providing a second strap and attaching the second end of the tether; and
    securing the tether to the limb via the second strap.

5. The method as in claim 4 further comprising a closure means for securing the ends of the second strap together.

6. The method as in claim 4 wherein the tether is comprised of a first section removably secured to a second section.

7. The method as in claim 1 wherein the housing is comprised of a first chamber and a second chamber fluidly sealed from the first chamber and such that the reel is disposed within the first chamber and a rotor is disposed within the second chamber such that the rotor is mechanically connected to the reel such that rotation of the reel causes rotation of the rotor and wherein the shear thickening non-Newtonian fluid is disposed within the second chamber.

* * * * *